US009089324B2

(12) United States Patent
McCaw et al.

(10) Patent No.: US 9,089,324 B2
(45) Date of Patent: Jul. 28, 2015

(54) SUTURE LOCKS AND SUTURE LOCK SYSTEMS

(75) Inventors: Trevor McCaw, Vancouver (CA); Elliot Y. K. Hong, Vancouver (CA); Steven W. Berhow, St. Michael, MN (US); Randall James Beyreis, Corcoran, MN (US)

(73) Assignee: AEGIS MEDICAL INNOVATIONS, INC., Vancouver, B.C. (CA)

( * ) Notice: Subject to any disclaimer, the term of this patent is extended or adjusted under 35 U.S.C. 154(b) by 606 days.

(21) Appl. No.: 13/318,967

(22) PCT Filed: May 4, 2010

(86) PCT No.: PCT/US2010/033481
§ 371 (c)(1),
(2), (4) Date: Jan. 18, 2012

(87) PCT Pub. No.: WO2010/129506
PCT Pub. Date: Nov. 11, 2010

(65) Prior Publication Data
US 2012/0109196 A1    May 3, 2012

Related U.S. Application Data

(60) Provisional application No. 61/175,199, filed on May 4, 2009.

(51) Int. Cl.
*A61B 17/04*    (2006.01)

(52) U.S. Cl.
CPC ..... *A61B 17/0487* (2013.01); *A61B 2017/0448* (2013.01)

(58) Field of Classification Search
CPC ............... A61B 2017/0446; A61B 2017/0448; A61B 2017/0451; A61B 2017/0462; A61B 2017/0619; A61B 2017/0456; A61B 2017/0458; A61B 2017/0454; A61B 17/0487
USPC .................................................. 606/228, 232
See application file for complete search history.

(56) References Cited

U.S. PATENT DOCUMENTS 5,356,435 A * 10/1994 Thein ............................ 606/232
5,370,661 A * 12/1994 Branch ......................... 606/232
(Continued)

FOREIGN PATENT DOCUMENTS

WO            00/30550 A1      6/2000
WO        2004/062506 A1      7/2004
(Continued)

OTHER PUBLICATIONS

International Preliminary Report on Patentability, issued Nov. 9, 2011, in Switzerland, Patent Application No. PCT/US2010/033481, filed May 4, 2010.

(Continued)

*Primary Examiner* — Alexander Orkin
(74) *Attorney, Agent, or Firm* — Mueting Raasch & Gebhardt, P.A.

(57) ABSTRACT

A suture lock including a first bore, a first restriction member extending into the first bore for restricting the movement of a suture element within the first bore, an optional second bore, and a second restriction member extending into the second bore for restricting the movement of a suture element. The suture lock may be provided in a system including a suture element. Methods of using the suture locks are also described.

22 Claims, 8 Drawing Sheets

(56) References Cited

U.S. PATENT DOCUMENTS

| | | | |
|---|---|---|---|
| 5,391,173 A * | 2/1995 | Wilk | 606/144 |
| 5,626,611 A * | 5/1997 | Liu et al. | 606/230 |
| 5,669,935 A | 9/1997 | Rosenman et al. | |
| 5,725,556 A * | 3/1998 | Moser et al. | 606/232 |
| 5,741,301 A | 4/1998 | Pagedas | |
| 5,885,294 A | 3/1999 | Pedlick et al. | |
| 6,015,428 A * | 1/2000 | Pagedas | 606/232 |
| 6,066,160 A | 5/2000 | Colvin et al. | |
| 6,197,043 B1 * | 3/2001 | Davidson | 606/228 |
| 2004/0236372 A1 * | 11/2004 | Anspach et al. | 606/232 |
| 2005/0143762 A1 * | 6/2005 | Paraschac et al. | 606/148 |
| 2005/0277957 A1 * | 12/2005 | Kuhns et al. | 606/148 |
| 2006/0106422 A1 * | 5/2006 | Del Rio et al. | 606/232 |
| 2006/0106423 A1 * | 5/2006 | Weisel et al. | 606/232 |
| 2008/0132944 A1 * | 6/2008 | Kress | 606/228 |
| 2010/0069925 A1 | 3/2010 | Friedman et al. | |

FOREIGN PATENT DOCUMENTS

| | | |
|---|---|---|
| WO | 2005/027754 A1 | 3/2005 |
| WO | 2008/036408 A2 | 3/2008 |

OTHER PUBLICATIONS

International Search Report, issued Jan. 21, 2011, in Korea, Patent Application No. PCT/US2010/033481, filed May 4, 2010.

Written Opinion, issued Jan. 21, 2011, in Korea, Patent Application No. PCT/US2010/033481, filed May 4, 2010.

* cited by examiner

SUTURE LOCKS AND SUTURE LOCK SYSTEMS

RELATED APPLICATION

This application is a U.S. National Stage Application of International Application No. PCT/US2010/033481, titled SUTURE LOCKS AND SUTURE LOCK SYSTEMS, filed on May 4, 2010, published in the English language on Nov. 11, 2010, as International Publication No. WO 2010/129506 A2, which claims the benefit under 35 U.S.C. §119 of U.S. Provisional Application Ser. No. 61/175,199 filed on May 4, 2009, entitled SUTURE LOCK AND SUTURE LOCK SYSTEMS, both of which are incorporated herein by reference in their entirety.

The disclosure herein relates generally to suture locks, e.g., used with suture lock systems and methods.

Suture locks including various features have previously been described. For example, a suture lock utilizing deflectable tongues has been described in U.S. Pat. No. 5,741,301 to Pagedas, issued on Apr. 21, 1998, and entitled "Self Locking Suture Lock." Further, for example, a suture retaining device using flexible fingers has been described in U.S. Pat. No. 5,669,935 to Rosenman et al., issued on Sep. 23, 1997, and entitled "One-Way Suture Retaining Device for Braided Sutures." Still further, for example, a suture securing device including movable cam members has been described in U.S. Pat. No. 6,066,160 to Colvin et al., issued on May 23, 2000, and entitled "Passive Knotless Suture Terminator for Use in Minimally Invasive Surgery and to Facilitate Standard Tissue Securing."

SUMMARY

Suture locks for restricting the movement of a suture element are described herein. The suture locks may be used to, e.g., tighten suture loops. The suture locks may include at least one bore and at least one restriction member extending into the bore, the restriction member positioned to engage a suture element extending through the bore to, e.g., restrict the movement of the suture element through the suture lock in at least one direction. Further, the suture locks described herein may be delivered through a single port of a delivery device through the use of axial force directed along a longitudinal axis extending through a delivery lumen (as opposed to, e.g., pulling on the tails of the suture element as would be required for, e.g., a suture knot, etc.).

In one aspect, some embodiments of a suture lock for restricting the movement of a suture element as described herein include: a body extending from a first end to a second end; a first bore extending along a first bore axis from the first end of the body to the second end of the body; and a first restriction member extending from a proximal end to a distal end along a first restriction member axis, wherein the proximal end is coupled to the body and the distal end extends into the first bore towards the first end of the body, wherein the first restriction member axis and the first bore axis form an included angle of about 75 degrees or less, and wherein the distal end restricts a suture element located within the first bore from moving within the first bore from the first end of the body to the second end of the body. In some embodiments, the body further comprises: a second bore extending along a second bore axis from the first end of the body to the second end of the body; and a second restriction member extending from a proximal end to a distal end along a second restriction member axis, wherein the proximal end is coupled to the body and the distal end extends into the second bore towards the first end of the body, wherein the second restriction member axis and the second bore axis form an included angle of about 75 degrees or less, and wherein the distal end restricts a suture element located within the second bore from moving within the second bore from the first end of the body to the second end of the body.

In some embodiments, the first restriction member axis and the first bore axis form an included angle of about 50 degrees or less and, where the second restriction member and second bore are provided, the second restriction member axis and the second bore axis form an included angle of about 50 degrees or less.

In some embodiments, the first restriction member axis and the first bore axis form an included angle of about 35 degrees or less and, where the second restriction member and second bore are provided, the second restriction member axis and the second bore axis form an included angle of about 35 degrees or less.

In another aspect, some embodiments of a suture lock for restricting the movement of a suture element as described herein include: a body extending from a first end to a second end; a first bore extending through the body from the first end of the body to the second end of the body; and a first restriction member extending from a proximal end to a distal end, wherein the proximal end is coupled to the body and the distal end extends into the first bore towards the first end, wherein the distal end is located at a first distance across the first bore that is about 50% or less than the width of the first bore, wherein the distal end restricts a suture element located within the first bore from moving within the first bore from the first end of the body to the second end of the body. In some embodiments, the body further comprises: a second bore extending through the body from the first end of the body to the second end of the body; and a second restriction member extending from a proximal end to a distal end, wherein the proximal end is coupled to the body and the distal end extends into the second bore towards the first end of the body, wherein the distal end is located at a second distance across the second bore that is about 50% or less than the width of the second bore, wherein the distal end restricts a suture element located within the second bore from moving within the second bore from the first end of the body to the second end of the body.

In some embodiments, the first distance is about 40% or less across the width of the first bore diameter and, where a second restriction member and second bore are provided, the second distance is about 40% or less across the width of the second bore.

In some embodiments, the first distance is about 33% or less across the width of the first bore diameter and, where a second restriction member and second bore are provided, the second distance is about 33% or less across the width of the second bore.

In some embodiments of the suture locks described herein, the first and/or the second restriction members are fixedly coupled to the body.

In some embodiments of the suture locks described herein, the first and/or the second restriction members are cylindrically shaped.

In some embodiments of the suture locks described herein, the distal end of the first and/or the second restriction members comprises a circular cone. In some embodiments, the apex of the circular cone of each of the distal ends of the first and the second restriction members is rounded.

In some embodiments of the suture locks described herein, the distal ends of the first and/or the second restriction members comprises an oblique cone.

In some embodiments of the suture locks described herein, the first and/or the second restriction members are substantially rigid.

In another aspect, some embodiments of a suture system as described herein include: a suture lock comprising a body extending from a first end to a second end; a first bore extending along a first bore axis from the first end of the body to the second end of the body, and a first restriction member extending from a proximal end to a distal end along a first restriction member axis, wherein the proximal end is coupled to the body and the distal end extends into the first bore towards the first end. The systems further comprise a suture element extending through the first bore of the suture lock, wherein the suture element comprises a ligating element extending from a first end of the suture element to a second end of the suture element, a lumen extending through the ligating element, and a control element located within and extending through the lumen of the ligating element, wherein the control element is incompressible. The distal end of the first restriction member extends into the ligating element of the suture element within the first bore to restrict the ligating element from moving within the first bore from the first end of the body to the second end of the body.

In some embodiments of the suture systems described herein, the suture lock further comprises a second bore extending through the body of the suture lock along a second bore axis from the first end of the body to the second end of the body; and a second restriction member extending from a proximal end to a distal end along a second restriction member axis, wherein the proximal end is coupled to the body and the distal end extends into the second bore towards the first end of the body. The suture element extends through the second bore such that the distal end of the first restriction member extends into the ligating element of the suture element within the second bore to restrict the ligating element from moving within the second bore from the first end of the body to the second end of the body.

In some embodiments of the suture systems described herein, the ligating element comprises braided material.

In some embodiments of the suture systems described herein, the distal ends of the first and/or the second restriction members pierce the ligating element of the suture element to restrict the ligating element of the suture element from moving from the first end to the second end of each of the first and the second bores.

In some embodiments of the suture systems described herein, the distal ends of the first and/or the second restriction members compresses the ligating element of the suture element within the first and/or second bores to restrict the ligating element of the suture element from moving from the first end to the second end in the first and/or the second bores.

In some embodiments of the suture systems described herein, the distal ends of the first and/or the second restriction members are located less than 0.010 inch or less away from the control element of the suture element.

In some embodiments of the suture systems described herein, the first restriction member axis and the first bore axis form an included angle of about 75 degrees or less, and wherein the distal end restricts a suture element located within the first bore from moving within the first bore from the first end of the body to the second end of the body. In some embodiments, the suture lock body further comprises a second bore extending along a second bore axis from the first end of the body to the second end of the body; and a second restriction member extending from a proximal end to a distal end along a second restriction member axis, wherein the proximal end is coupled to the body and the distal end extends into the second bore towards the first end of the body, and wherein the second restriction member axis and the second bore axis form an included angle of about 75 degrees or less; wherein the distal end restricts a suture element located within the second bore from moving within the second bore from the first end of the body to the second end of the body.

In some embodiments of the suture systems described herein, the distal end of the first restriction member is located at a first distance across the first bore that is about 50% or less than the width of the first bore, wherein the distal end of the first restriction member restricts a suture element located within the first bore from moving within the first bore from the first end of the body to the second end of the body. In some embodiments, the suture lock body further comprises a second bore extending through the body from the first end of the body to the second end of the body; and a second restriction member extending from a proximal end to a distal end, wherein the proximal end is coupled to the body and the distal end extends into the second bore towards the first end of the body, and wherein the distal end is located at a second distance across the second bore that is about 50% or less than the width of the second bore; wherein the distal end of the second restriction member restricts a suture element located within the second bore from moving within the second bore from the first end of the body to the second end of the body.

The above summary is not intended to describe each embodiment or every implementation of the suture lock devices and systems discussed herein. Advantages, together with a more complete understanding, will become apparent and appreciated by referring to the following detailed description and claims taken in conjunction with the accompanying drawings.

The figures are rendered primarily for clarity and, as a result, are not necessarily drawn to scale.

DETAILED DESCRIPTION OF ILLUSTRATIVE EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of this disclosure.

Exemplary systems and methods shall generally be described with reference to FIGS. 1-12. Elements from one embodiment may be used in combination with elements of the other embodiments, and that the possible embodiments of such apparatus using combinations of features set forth herein is not limited to the specific embodiments shown in the figures and/or described herein. Further, the embodiments described herein will include many elements that are not necessarily shown to scale. Further, the size and shape of various elements herein may be modified without departing from the scope of the present disclosure, although one or more shapes and sizes, or types of elements, may be advantageous over others.

As used herein, "a," "an," "the," "at least one," and "one or more" are used interchangeably. The term "and/or" (if used) means one or all of the listed elements or a combination of any two or more of the listed elements.

Further, as used herein, the term "anatomical structure" may be defined as any anatomical and/or pathological structure, e.g., the left atrial appendage (LAA), the gallbladder, the GI appendage, diverticula, fallopian tubes, ovaries, vascular aneurysms, any pedunculated structure or mass, muscles, bones, vascular structures, etc.

Figure 1:
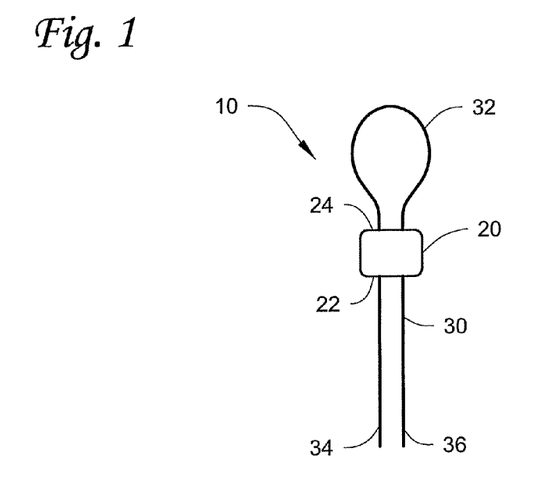
FIG. 1 depicts an exemplary suture lock system.

FIG. 1 depicts an exemplary suture lock system 10. The system 10 may include a suture lock 20 and a suture element 30. The suture lock system 10 may be used, e.g., to fasten, approximate, and/or ligate anatomical structures and may be configured for catheter, endoscopic, and/or open surgical procedures on any site within a patient or animal.

The suture lock 20 extends from a first end 22 to a second end 24 and receives the suture element 30 such that the suture lock 20 restricts the movement of the suture element 30 in at least one direction. For example, in this embodiment, the suture element 30 is doubled through the suture lock 20 forming a suture loop 32. The suture loop 32 may be reduced in size, e.g., tightened around an anatomical structure, by pulling the ends 34, 36 of the suture element 30 away from the suture lock 20 while holding the suture lock 20 stationary, by pushing on the suture lock 20 towards the suture loop 23 while holding the ends 34, 36 of the suture element 30 stationary, or by simultaneously pushing on the suture lock 20 towards the suture loop 32 and pulling the ends 34, 36 of the suture element 30 away from the suture lock 20.

The loop 32 of the suture element 30 may take any suitable shape and size. For example, the loop 32 may have an essentially circular or oval shape, or may have an irregular shape, e.g., to follow the curve of the heart. Further, the loop 32 may have, e.g., a maximum cross-loop dimension from about 0.5 cm to about 4 cm (e.g., from about 0.7 cm to about 3.5 cm, from about 1.0 cm to about 2.5 cm, or from about 1.5 cm to about 2.0 cm).

The suture element 30 may be take any suitable form, e.g., a monofilament and/or braided suture, and may include any suitable material or combination of materials such as, e.g., polyester, PTFE, polyethylene, nylon, polypropylene, metal (e.g., stainless steel, spring steel, Nitinol, etc.) and/or any other suitable material used in surgical applications. Further, the suture element 30 may be constructed of absorbable materials (such that, e.g., the suture element may break-down over time when placed within a body without intervention) or non-absorbable. In at least one embodiment, the suture element 30 may include shape memory materials such as, e.g., Nitinol, shape memory polymers, etc.

The suture lock system 10 and/or other suture locks/suture elements described herein may be incorporated and/or utilized with any other medical instrument as would be recognized by one having ordinary skill in the art, e.g., delivery catheters, push members, endoscopes, suction catheters, forceps, cryogenic-tipped catheters, etc. For example, suture lock system 10 and/or other suture locks/suture elements described herein may incorporated and/or utilized with the sutures and other elements described in International Publication No. WO/2008/036408 entitled DEVICES FOR LIGATING ANATOMICAL STRUCTURES; U.S. patent application Ser. No. 12/442,294 filed Mar. 20, 2009; and U.S. Provisional Patent Application No. 61/106,761 entitled "TISSUE LIGATION DEVICES AND METHODS."

Figure 2:
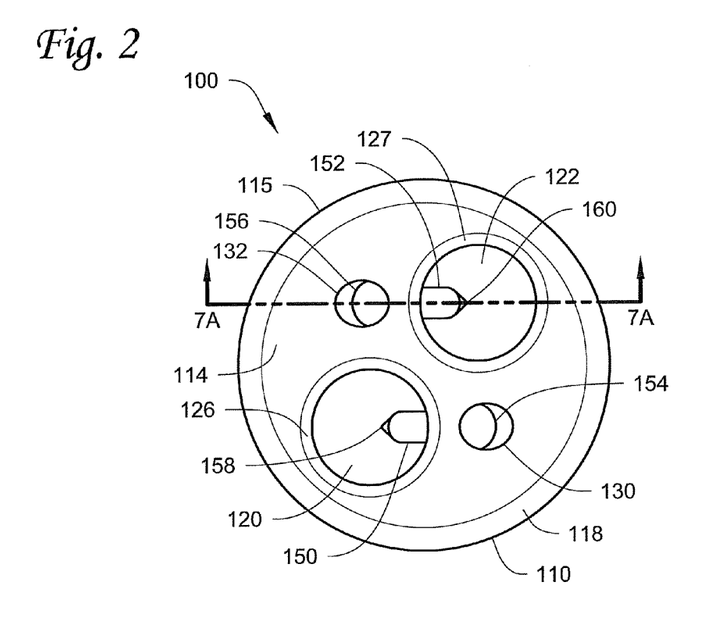
FIG. 2 is a top view of an exemplary suture lock.
Figure 3:
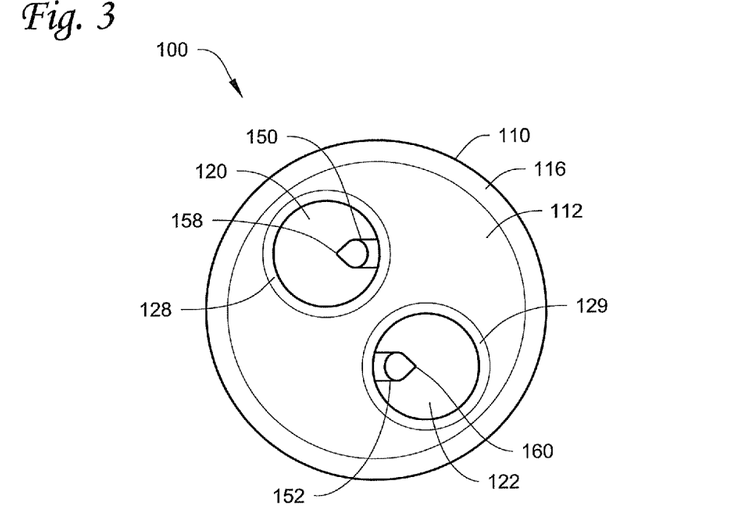
FIG. 3 is bottom view of the suture lock of FIG. 2.
Figure 4:
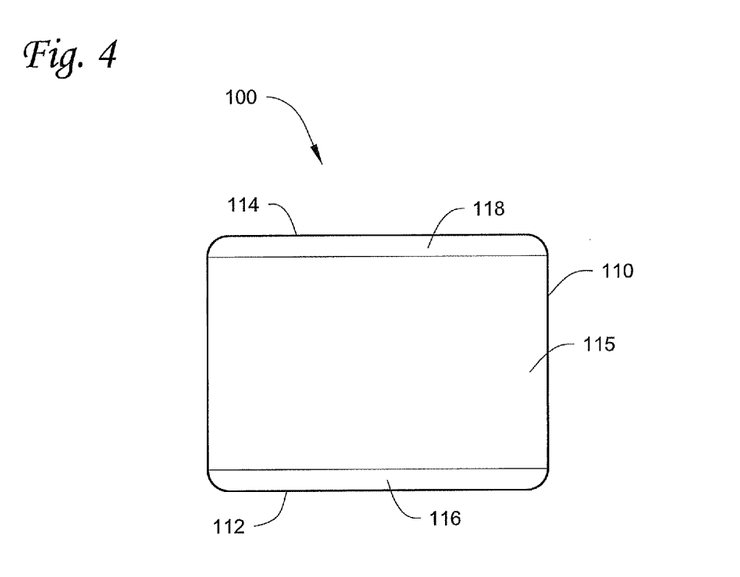
FIG. 4 is a side view of the suture lock of FIG. 2.

FIGS. 2-7 illustrate, in more detail, one embodiment of a suture lock 100. The suture lock 100 includes a body 110 extending from a first end 112 (FIGS. 3-4) to a second end 114 (FIGS. 2 & 4). In the embodiment depicted, the body 110 has a cylindrical outer surface 115 that may, e.g., conform to the shape of a lumen of a delivery catheter. In other embodiment, for example, the body 110 may have an outer surface provided in any suitable shape, e.g., box-shaped, triangular, oval-shaped, crescent-shaped, spherical, cylindrical, etc. Further, each end 112, 114 of the body 110 may include a beveled (e.g., rounded, etc.) edge 116, 118, respectively, between the outer surface 115 and the end 112, 114 to, e.g., assist the movement of the body 110 through a delivery catheter, minimize erosion of the suture material or tissue, etc. Still further, in at least one embodiment, the body 110 may have an outer shape that corresponds to the shape of a delivery lumen in a delivery device used to deliver the body 110 (e.g., a lock-and-key relationship) such that the body 110 may, for example, be restricted from rotation about a longitudinal axis extending through the delivery lumen in the delivery device.

The body 110 may be constructed of any suitable material or combination of materials such as, e.g., titanium, stainless steel, an organic polymer (e.g., PEEK), polyester, PTFE, polyethylene, nylon, polypropylene, and/or any other suitable material that can be used in surgical applications. Further, the material of the body 110 may be constructed of materials that are absorbable (e.g., material that may break-down over time without intervention when placed within a body) or non-absorbable.

The body 110 includes first bore 120 extending from the first end 112 to the second end 114 and a second bore 122 extending from the first end 112 to the second end 114. Each of the bores 120, 122 may extend along an axis that is generally parallel to the outer surface 115 of the body 110. Although each of the bores 120, 122 in this embodiment are aligned with each other (e.g., parallel or substantially parallel) and the outer surface 115, in other embodiments, e.g., the bores may not be aligned with each other and/or to an outer surface of the body 110. In the embodiment depicted in FIGS. 2-7C, the bores 120, 122 have a circular cross section (e.g., forming a cylindrical body). In other embodiments, however, the bores may have any cross section, e.g., a square, rectangle, octagon, etc. Further, each of the bores 120, 122 may include beveled (e.g., rounded) corners 126, 128, 127, 129, respectively, to, e.g., facilitate the movement of a suture element through the bores 120, 122.

In at least one embodiment, the body of the suture lock may include a single bore extending from the first end to the second end. A suture element may extend through the bore and may be attached to a portion of the body of the suture lock such that a loop is formed. In this embodiment, the loop may be reduced in size, e.g., tightened around an anatomical structure, by pulling the single end of the suture element away from the suture lock, pushing the suture lock towards the loop while holding the single end of the suture element stationary, or a combination of the two methods. In connection with FIG. 1, for example, such a suture lock 20 may include a suture loop 32, but would include a suture element 30 in which only one end, e.g., end 36 extends out of the suture lock 20. The other end of the suture element 30 may terminate within the suture lock or be otherwise secured to the suture lock 20 such that only end 36 is available for manipulation to tighten the loop 32.

In some embodiments, the suture lock 20 may include two bores as described herein and the other end (i.e., end 34 in FIG. 1) may be removed after the suture element 30 is positioned within the suture lock 20 such that only end 36 extends from the suture lock 20. As a result, only end 36 of the suture element 30 would be available for manipulation to tighten the loop 32.

Further, in at least one embodiment, the body of the suture lock may include a single bore within which both ends of the suture element may extend therethrough. One potential example of such a construction may be depicted in, e.g., FIG. 9.

The suture lock 110 further includes a first restriction member 150 extending from a proximal end 154 to a distal end 158 and a second restriction member 152 extending from a proximal end 156 to a distal end 160. Although the depicted embodiment includes two restriction members and two bores (with one restriction member in each bore), other embodiments may include two or more restriction members within at least one bore in a suture lock.

The restriction members 150, 152 may be, e.g., cylindrically shaped. In other embodiments, the restriction member 150, 152 may be any suitable shape and/or size. The proximal ends 154, 156 of the restriction members 150, 152 are coupled to the body 110. In at least one embodiment, the proximal ends 154, 156 of the restriction members 150, 152 are fixedly coupled to the body 110. As used herein, teen "fixedly coupled" may be defined as permanently attached under normal use conditions. Further, in at least one embodiment, the proximal ends 154, 156 of the restriction members 150, 152 are laser welded to the body 110. In other embodiments, the proximal ends 154, 156 of the restriction members 150, 152 may be adhered to, compression fit within, molded with, welded within, and/or threaded within the body 110. For example, the restriction members 150, 152 and the body 110 may be molded as a single, integral article which may or may not be constructed of a homogeneous mass of material, insert molded (in which, e.g., the restriction members may be constructed of a different material as compared to the body 110), etc.

Figure 5:
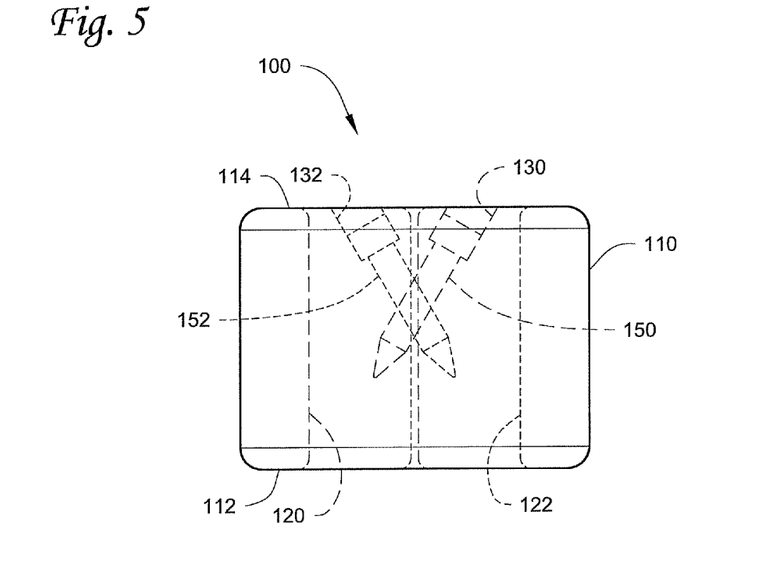
FIG. 5 is a partially transparent side view of the suture lock of FIG. 2.
Figure 6:
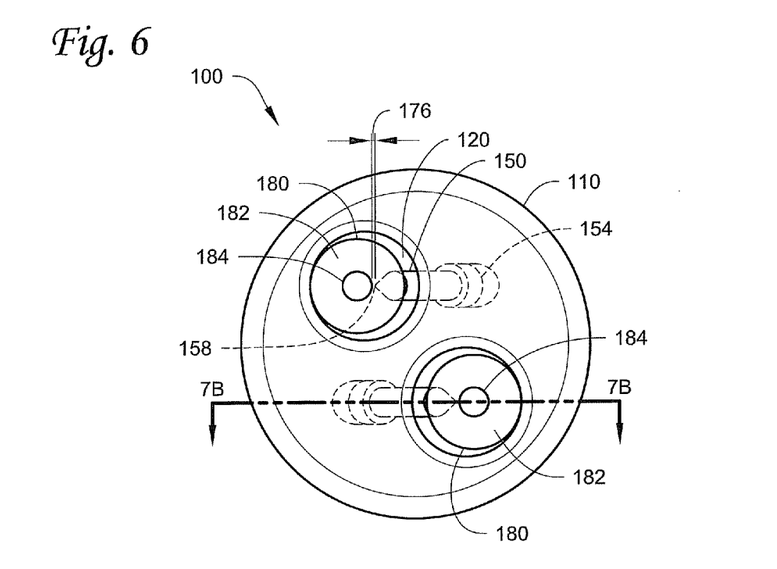
FIG. 6 is a partially transparent bottom view of the suture lock of FIG. 2 including a suture element.
Figure 7A:
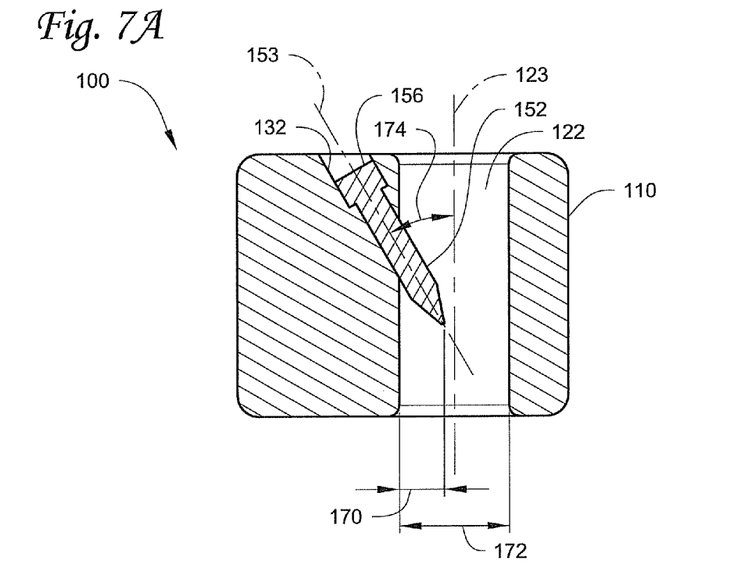
FIG. 7A is a cross sectional view of the suture lock of FIG. 2 taken along line 7A-7A.

In the embodiment depicted, the body 110 defines a first restriction member aperture 130 and a second restriction member aperture 132 for the first restriction member 150 and the second restriction member 152 to be inserted and coupled within, e.g., below the second end 114 of the body 110 (FIGS. 5 & 7A). In other embodiments, the restriction members 150, 152 may be secured flush with a surface (e.g., the surface of the second end 114) of the body 110.

The restriction members 150, 152 may be constructed of any suitable material or a combination of materials such as, e.g., titanium, stainless steel, PEEK, polyester, PTFE, polyethylene, nylon, polypropylene, and/or any other suitable material that can be used in surgical applications. Further, the restriction members 150, 152 may be a substantially rigid material, a flexible material, or a combination of flexible and rigid materials. Further, the material of the restriction members 150, 152 may be constructed of materials that are absorbable (e.g., material that may break-down over time without intervention when placed within a body) or non-absorbable.

The distal ends 158, 160 of the restriction members 150, 152 may extend into the first and second bore 120, 122, respectively, to contact a suture element 180 located therein (FIGS. 6 & 7B-7C) to permit the suture element 180 to move in a direction and to restrict the suture element 180 from moving in the opposite direction (e.g., to permit movement from the second end 24 to the first end 22 and to restrict movement from the first end 22 to the second end 24). In other embodiments, the restriction members 150, 152 may be configured oppositely such that each bore permits/restricts movement of the suture element 180 in opposite directions (e.g., the first bore may restrict movement of the suture element located therein from moving from a first end to a second of the suture lock and the second bore may restrict movement of the suture element located therein from moving from the second end to the first of the suture lock). The restriction members 150, 152 may be located anywhere within the body 110 of the suture lock 100 such that the distal ends 158, 160 extend into a location within the bores 120, 122, respectively so as to the contact a suture element 180 located therein.

In some embodiments, the restriction members may be substantially rigid. In other words, the restriction members may not appreciably deflect when a suture element is located in a bore into which the restriction element protrudes. Although some minimal deflection of the restriction member may occur, that deflection is not required and/or planned as a part of the functioning of the suture lock.

The suture lock 100 may be used in any combination with many different suture elements. In the embodiment depicted in FIGS. 6 & 7B, the suture element 180 includes a ligating element 182 defining a lumen and a core 184 extending through the lumen of the ligating element 182. The ligating element 182 may be take any suitable form, e.g., a monofilament and/or braided elements and may include any suitable material or combination of materials such as, e.g., polyester, PTFE, polyethylene, nylon, polypropylene, metal, and/or any other suitable material that can be used in surgical applications. Further, the material of the ligating element 182 may be absorbable (e.g., material that may break-down within a body without intervention) or non-absorbable.

The core 184 may be constructed of any suitable material or combination of materials e.g., metals (e.g., Nitinol, etc.), polymers (e.g., polyester, PTFE, polyethylene, nylon, polypropylene, etc.), and/or any other suitable material or materials that can be used in surgical applications. In some embodiments, the core 184 may be substantially incompressible under normal use conditions where the compression force is applied by the restriction members of the suture locks described herein (e.g., the core 184 may be about 1% or less, about 5% or less, about 10% or less, or about 25% or less compressible).

Further, the distal ends 158, 160 of the restriction members 150, 152 may extend into the space otherwise occupied by ligating element 182 of the suture element 180 to restrict the ligating element 182 of the suture element 180 from moving through the bore in a direction, e.g., from the first end 112 to the second end 114. Depending on the material and/or type of the ligating element 182 utilized (e.g., braided or monofilament/polyethylene or nylon), the distal ends 158, 160 of the restriction members 150, 152 either compress, deform, puncture, pierce, adhere to, and/or perforate the ligating element 182. In one or more embodiments, the distal ends 158, 160 of the restriction members 150, 152 may restrict the ligating element 182 from moving without damaging (e.g., cutting, fraying, tearing, stressing, splitting, etc.) the ligating element 182. For example, the ligating element 182 may be braided and the distal ends 158, 160 of the restriction members 150, 152 may extend into the interstices of the filaments forming the braid to restrict a braided ligating element 182 from movement in a direction, e.g., movement from the first end 112 to the second 114.

It may be preferred, however, that the distal ends 158, 160 of the restriction members 150, 152 do not extend into or otherwise interact with the core 184 of the suture element 180 in a manner that prevents removal of the core 184. As a result, the core 184 may be removed from the suture element 180 while the ligating element 182 remains fixed within the suture lock 100.

Some additional examples of a variety of suture elements that may potentially be incorporated in and/or utilized with the suture locks described herein are described in International Publication No. WO/2008/036408 entitled DEVICES AND METHODS FOR LIGATING ANATOMICAL STRUCTURES; U.S. patent application Ser. No. 12/442,294 filed Mar. 20, 2009; and U.S. Provisional Patent Application No. 61/106,761 entitled "TISSUE LIGATION DEVICES AND METHODS."

The restriction members 150, 152 may extend to different locations across the bores 120, 122 of the body 110. For example, FIG. 7A depicts the second restriction member 152 extending distance 170 within the bore 122. Distance 170 is measured perpendicular to the axis 123 of the bore 122. At the upper end, the distance 170 may be, e.g., about 75% or less, about 60% or less, about 50% or less, about 40% or less, or about 33% or less of the width 172 of the bore 122 (i.e., width 172 of the bore 122 is measured perpendicular to the axis 123 of the bore 122). At the lower end, the distance 170 may, for example, be about 5% or more, about 15% or more, about 25% or more, about 33% or more, 40%, or about 50% or more of the width 172 of the bore 122 (i.e., width 172 of the bore 122 is measured perpendicular to the axis 123 of the bore 122). Further, in at least one embodiment, the distance 170 may be nearly 100% of the width 172 of the bore 122 such that, e.g., the restriction members 150, 152 are configured to deflect when contacting a suture element located within the bore.

Further, the restriction members 150, 152, may extend into the bores 120, 122 of the body 110 at different angles. For example, FIG. 7A depicts second restriction member 152 extending along axis 153, which forms an included angle 174 with the bore axis 123. As used herein, the term "included angle" may be defined as the internal angle between two lines. At the upper end, the included angle 174 may be, e.g., about 75 degrees or less, about 50 degrees or less, about 35 degrees or less, or about 30 degrees or less. At the lower end, the included angle 174 may be, for example, about 5 degrees or more, about 15 degrees or more, about 25 degrees or more, about 30 degrees or more, or about 40 degrees or more. In at least one embodiment, the include angle 174 is about 35 degrees.

Figure 7B:
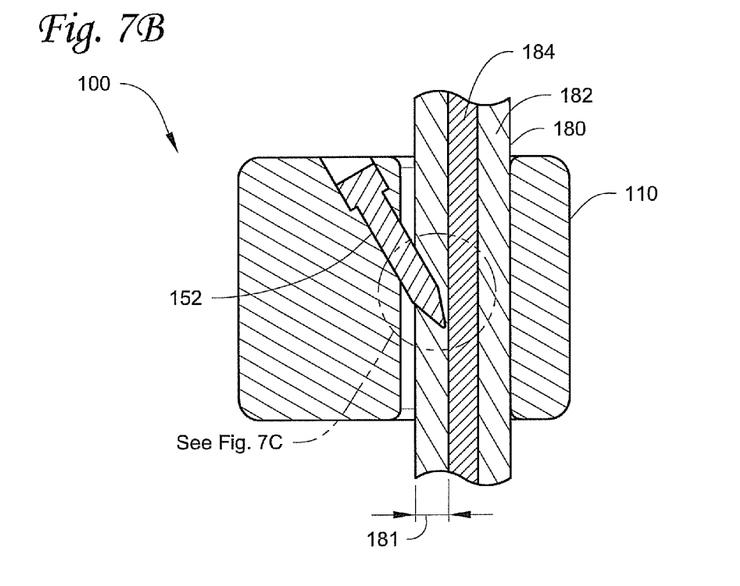
FIG. 7B is a cross sectional view of the suture lock including the suture element of FIG. 6 taken along line 7B-7B.
Figure 7C:
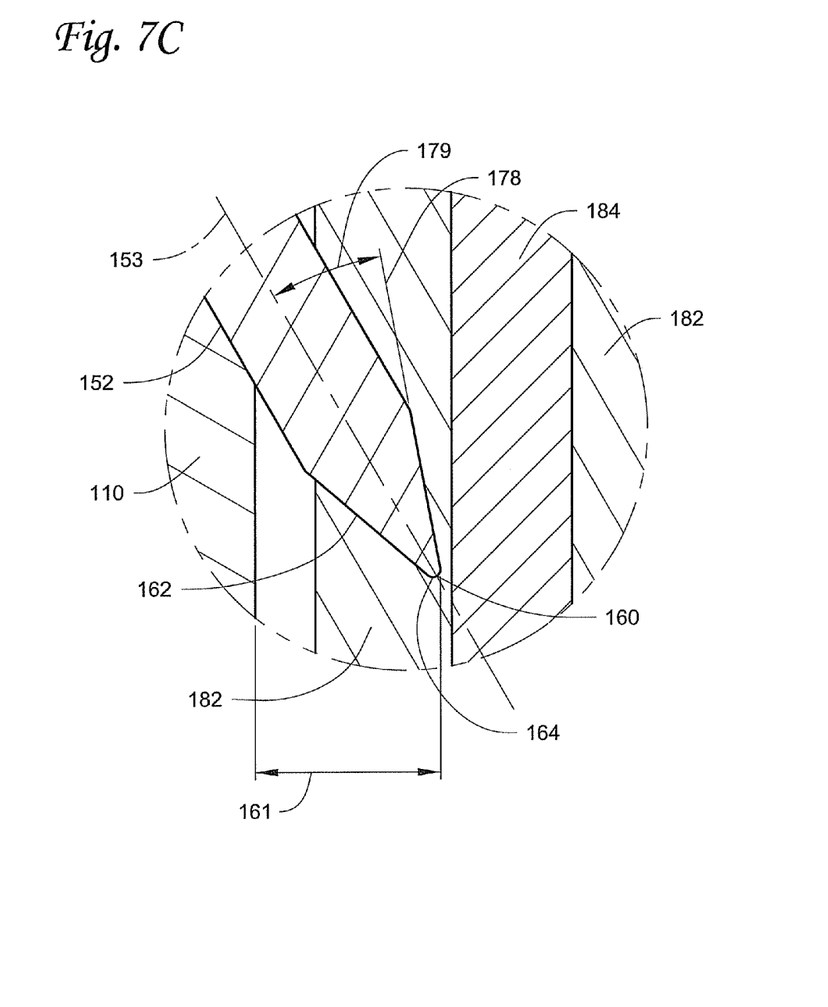
FIG. 7C is an enlarged, cross sectional view of the dashed circle portion of the FIG. 7B.

Still further, the distance the restriction members 150, 152 extend into the bores 120, 122 of the body 110 may be defined by the distance the restriction members 150, 152 extend into the suture element 180 (see FIG. 7C). The distal end 160 of the restriction member 152 may extend distance 161 into the suture element 180. At the upper end, distance 161 may be, e.g., about 100% or less, about 95% or less, about 90% or less, about 75% or less, or about 66% or less of the width 181 of the wall of the ligating element 182 of the suture element 180. At the lower end, distance 161 may be, e.g., about 25% or more, about 33% or more, about 50% or more, about 66% or more, about 75% or more, or about 90% or more of the width 181 of the wall of the ligating element 182 of the suture element 180. In other words, the distal end 160 of the restriction member 152 may extend into the wall, e.g., almost entirely through the wall, of the ligating element 182 without directly engaging and/or contacting the core 184. Further, in at least one embodiment, the distance 176 between the distal end 158 of the restriction member 150 (which may be similar the restriction member 152) and the core 184 may be, e.g., about 0.010 inch or less, although other distances (e.g., 0.005 inch or less) may be used in other embodiments (see FIG. 6)

The distal ends 158, 160 of the restriction members 150, 152 may have various shapes. For example, as depicted, the distal ends 158, 160 are in the form of a circular cone 162 with a rounded tip 164. In other embodiments, the distal ends 158, 160 may be in the form of an oblique cone, a flat end, a dome, a beveled end, sharp point, concave cone, helix, concave dome, sharp flat edge, roughen edge (e.g., to grip a suture element), etc. Further, in at least one embodiment, the distal ends 158, 160 may include an adhesive to, e.g., adhere a suture element to a restriction member (to, e.g., further restrict the movement of the suture element relative to the restriction member).

Further, the pitch of the shape of the distal ends 158, 160 of the restriction members 150, 152 may assist in restricting the suture element 180 within the bores 120, 122. FIG. 7C is an enlarged, cross sectional view of the dashed circle portion 171 of the FIG. 7B showing the distal end 160 of the restriction member 152 engaging the suture element 180. Line 178 extends along the outer surface of the conical end 162 and forms an angle 179 with the axis 153 of the restriction member 160. In one or more embodiments, the angle 179 may be less than the included angle 174 formed by the intersection of the axis 153 and the bore axis 123. At the upper end, the angle 179 may be, for example, about 75 degrees or less, about 50 degrees or less, about 35 degrees or less, or about 30 degrees or less. At the lower end, the angle 179 may be, for example, about 5 degrees or more, about 15 degrees or more, about 25 degrees or more, about 30 degrees or more, or about 40 degrees or more. In at least one embodiment, the angle 179 is about 33 degrees.

Figure 8:
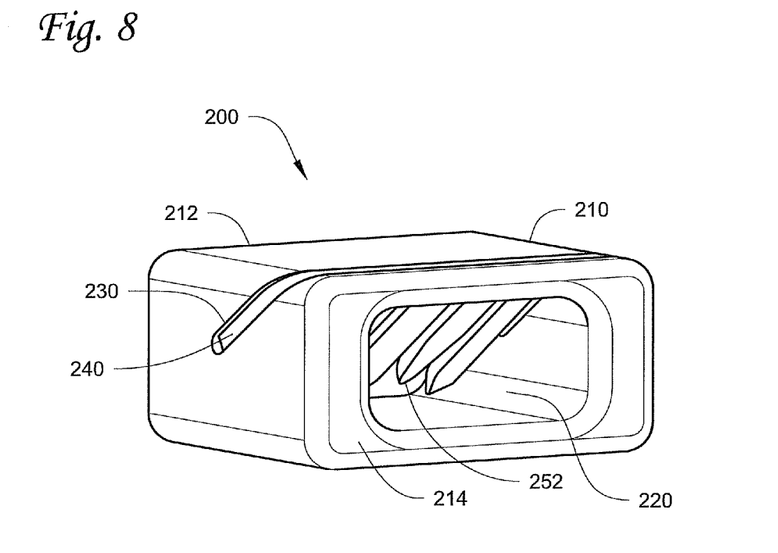
FIG. 8 is a perspective view of another exemplary suture lock.
Figure 9:
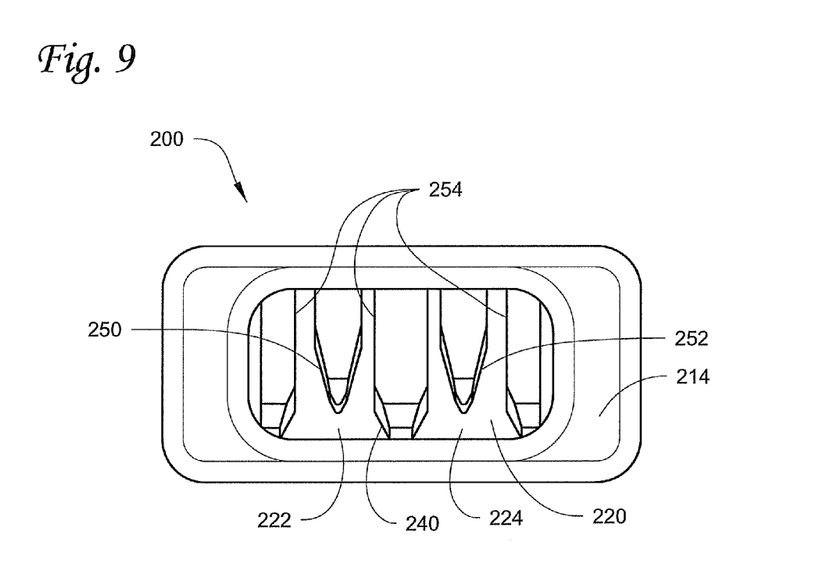
FIG. 9 is a top view of the suture lock of FIG. 8.

FIGS. 8-9 depict another exemplary suture lock 200. Suture lock 200 may be similar to the suture lock 100 previously described herein and, as such, may include any one or more of the features and/or properties described with respect to suture lock 100.

Suture lock 200 may include a body 210 extending from a first end 212 to a second end 214 and a restriction body 240. In this embodiment, the body 210 is rectangular. In other embodiments, however, the suture lock 200 may have any shape. The suture lock 200 may further define an opening 220 extending from the first end 212 to the second end 214.

The restriction body 240 of the suture lock 200 may include a first restriction member 250 and a second restriction member 252 that may operate in a similar manner and may be formed of similar material or combination of materials as the restriction members 150, 152 of the suture lock 100 described herein. For example, the restriction members 250, 252 may restrict a suture element from moving through the opening 220 in a direction (e.g., from the first end 212 to the second end 214 of the suture lock 200) and permit a suture element from moving through the opening 220 in the opposite direction (e.g., from the second end 214 to the first end 212 of the suture lock 200). Further, for example, the tips of the restriction members 250, 252 may be shaped as circular cones, etc. (as described herein).

The restriction body 240 may further include elongated members 254 that extend within the opening 220 and define a first passage 222 and a second passage 224 through the opening 220 through which, e.g., a suture element may extend thereby engaging the restriction members 250, 252. Although in this embodiment, the restriction body 240 includes three elongated members 254 and two restriction members 250, 252 and defines two passages 222, 224, in other embodiments, the restriction body 240 may include two elongated members and one restriction member and define a single passage or include more than three elongated members and two restriction members and define more than two passages. Further, the elongated members 254 may extend across the opening 220 and engage and/or contact the opposite inner wall defining the opening 220. In other embodiments, the elongated members 254 may extend across the opening 220 to a distance (e.g., completely or nearly completely) that does not allow a suture element to pass through (i.e., the elongated members 254 may essentially divide the opening 220 into separate passages 222 and 224).

Further, the restriction body 240 in this embodiment may be substantially flat in shape and may be fixedly coupled within a channel 230 defined in the body 210. In other embodiments, the restriction body 240 may have any suitable shape, e.g., curved, etc. Further, in one or more embodiments, the restriction body 240 may be formed (e.g., stamped, molded, machined, laser-cut, etc.) from a flat sheet of bulk material, e.g., a metal or metal alloy. Still further, the restriction body 240 may be fixedly coupled with the channel 230 by, e.g., adhering, welding, interference fit, etc. Further, the distal ends of the restriction members 250, 252 may be in the form of a rounded tip, an oblique cone, a flat end, a dome, a beveled end, sharp point, concave cone, helix, concave dome, sharp flat edge, roughen edge (e.g., to grip a suture element), etc. Further, in at least one embodiment, the distal ends of the restriction members 250, 252 may include an adhesive to, e.g., adhere a suture element to a restriction member (to, e.g., further restrict the movement of the suture element relative to the restriction member).

Figure 10:
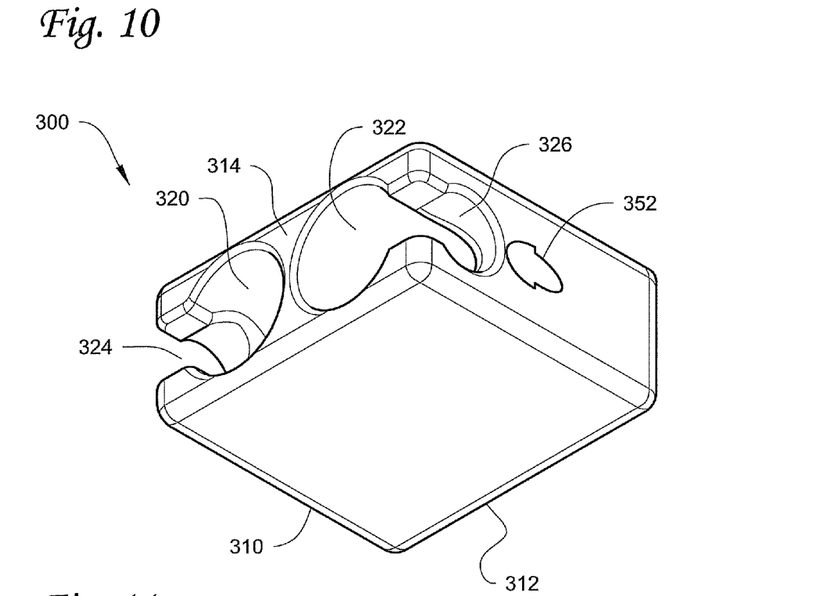
FIG. 10 is a perspective view of still another exemplary suture lock.
Figure 11:
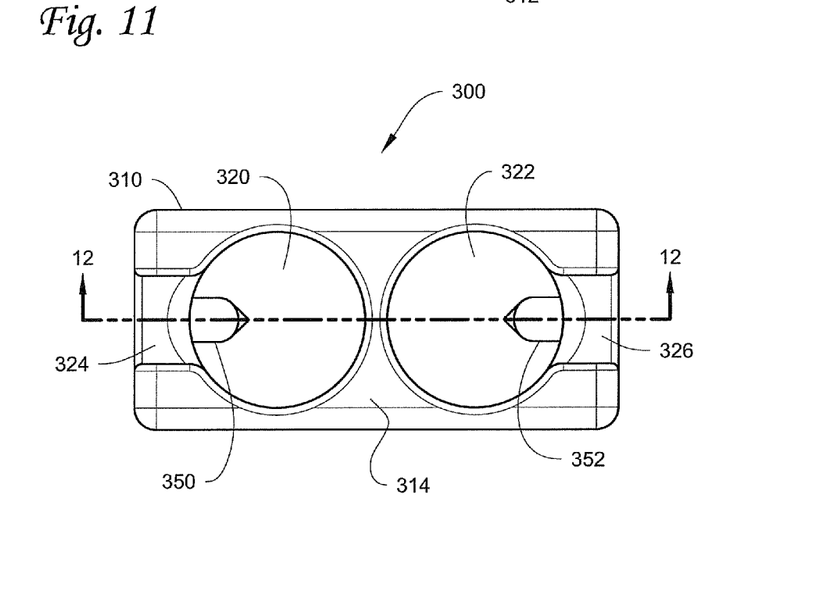
FIG. 11 is a top view of the suture lock of FIG. 10.
Figure 12:
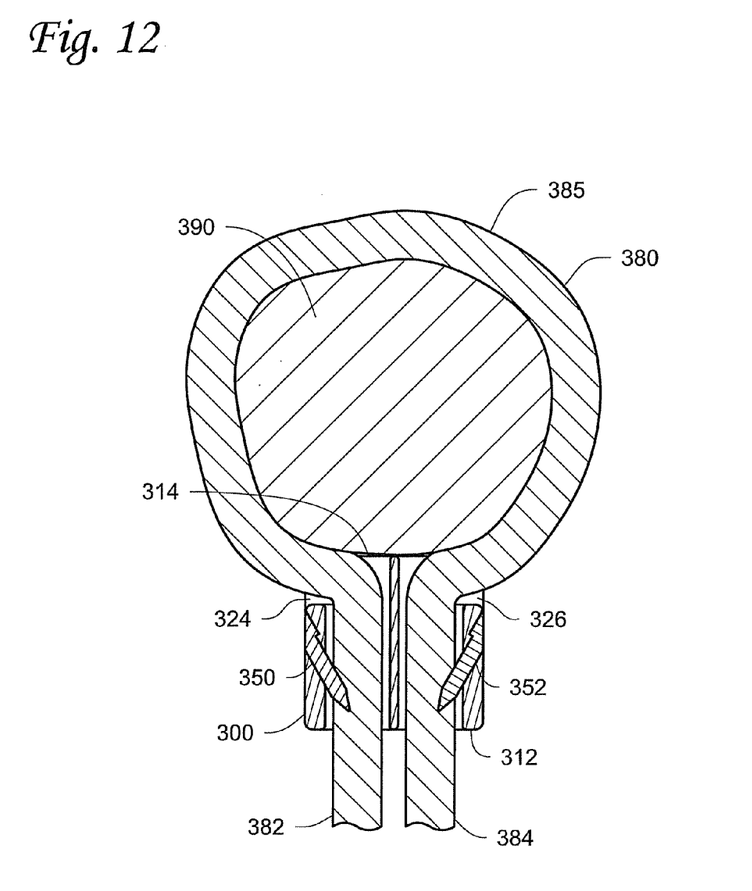
FIG. 12 is a cross sectional view of the suture lock of FIG. 11 taken along 12-12, a suture element, and an anatomical structure.

FIGS. 10-12 depict still another exemplary suture lock 300. Suture lock 300 may be similar to the suture locks 100, 200 described herein and, as such, may include any one or more of the features and/or properties described with respect to suture locks 100, 200.

Suture lock 300 may include a body 310 extending from a first end 312 to a second end 314. In this embodiment, the body 310 is rectangular. In other embodiments, however, the suture lock 300 may have any suitable shape.

The suture lock 300 may define a first bore 320 and a second bore 322, each extending from the first end 312 to the second end 314. Each of the first bore 320 and second bore 322 may receive a suture element to permit movement of the suture element in one direction (e.g., from the second end 314 to the first end 312) and to restrict movement of the suture element in another direction (e.g., from the first end 312 to the second end 314). The suture lock 300 further includes a first restriction member 350 and a second restriction member 352 that may operate in a similar manner and may be formed of similar material or materials as the restrictions members 150, 152 of the suture lock 100 described previously herein. For example, the restriction members 350, 352 may restrict a suture element from moving through the first bore 320 and the second bore 322 in a direction (e.g., from the first end 312 to the second end 314 of the suture lock 300). Each restriction member 350, 352 may be fixedly coupled to the body 310.

The suture lock 300 may further define a first notch 324 and a second notch 326 located proximate the first bore 320 and second bore 322, respectively, in which a suture element may be located within to, e.g., at least partially restrict the movement of the suture element through the suture lock 300. For example, the inner surface of the first notch 324 and the second notch 326 may contact, engage, compress, pinch, etc. a suture element located therein so that its movement is restricted.

In at least one embodiment, the notches 324, 326 may be configured (e.g., sized and/or shaped) such that the suture element may enter each of the notches 324, 326 when the suture element is tightened around, e.g., an anatomical object, at a selected force (e.g., a maximum force). In this example, the notches 324, 326 may act as an over-tightening prevention mechanism.

For example, FIG. 12 depicts a suture element 380 extending through the suture lock 300. The suture element 380 forms a suture loop 385 that may, e.g., as shown, extend around or through an anatomical structure 390. The suture loop 385 may be reduced in size around the anatomical structure 390 by pulling the ends 382, 384 of the suture element 380 and holding the suture lock 300 stationary thereby moving the suture element 380 through the suture lock 300 (e.g., in the permitted direction, from the second end 314 to the first end 312). As shown in FIG. 12, the suture loop 385 is already reduced in size around the anatomical structure 390 (e.g., selectively tightened around the anatomical structure 390) and a portion of the suture 380 has moved into each of the first notch 324 and the second notch 326, respectively, (e.g., due to an operator pulling the ends 382, 384 of the suture element 380 thereby reducing the size of the suture loop 385 around the anatomical structure 390 which may contact the second end 314 of the suture lock 300 against the anatomical structure 390 and may move the suture element 380 into the notches 382, 384). In one or more embodiments, the suture element 180 may be formed of sufficiently resilient material such that, e.g., the resilience of the suture loop 385 of the suture element 380 may move the suture element 380 into the notches 324, 326 when reduced in size (e.g., tightened).

The first and the second notch 324, 326 may assist in restricting the movement of the suture element by, e.g., contacting, engaging, compressing, pinching, etc. the suture element 380. Further, the notches 324, 326 may allow the suture element 380 to extend in a direction that is substantially perpendicular to the bores 320, 324 from the second end 314 of the suture lock 300. That change in direction may assist in creating a conformal suture loop 385 around the anatomical structure 390 and/or may reduce further axial movement of the suture lock 300. Still further, the second end 314 of the suture lock 300 may contact the anatomical structure 390 thereby effectively becoming a portion of the suture loop 385.

The complete disclosure of the patents, patent documents, and publications identified herein are incorporated by reference in their entirety as if each were individually incorporated.

Illustrative embodiments of suture locks and suture lock systems have been discussed and reference has been made to possible variations within the scope of this invention. These and other variations and modifications will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A suture system comprising:
   a suture lock comprising:
      a body extending from a first end to a second end;
      a first bore extending along a first bore axis from the first end of the body to the second end of the body, and a first restriction member extending from a proximal end to a distal end along a first restriction member axis, wherein the proximal end is coupled to the body and the distal end extends into the first bore towards the first end; and
a suture element extending through the first bore of the suture lock, wherein the suture element comprises:
a ligating element extending from a first end of the suture element to a second end of the suture element,
a lumen extending through the ligating element, and
a control element located within and extending through the lumen of the ligating element, wherein the control element is incompressible,
wherein the distal end of the first restriction member extends into an interstice between filaments forming the ligating element of the suture element within the first bore to restrict the ligating element from moving within the first bore from the first end of the body to the second end of the body.

2. The system of claim 1, wherein the first restriction member axis and the first bore axis form an included angle of about 50 degrees or less.

3. The system of claim 1, wherein the first restriction member axis and the first bore axis form an included angle of about 35 degrees or less.

4. The system of claim 1, wherein the first restriction member is fixedly coupled to the body.

5. The system of claim 1, wherein the first restriction member is cylindrically shaped.

6. The system of claim 1, wherein the distal end of the first restriction member comprises a circular cone.

7. The system of claim 6, wherein an apex of the circular cone of the distal end of the first restriction member is rounded.

8. The system of claim 1, wherein the distal end of the first restriction member comprises an oblique cone.

9. The system of claim 1, wherein the first restriction member is substantially rigid.

10. The system of claim 1, wherein the system further comprises:
a second bore extending through the body of the suture lock along a second bore axis from the first end of the body to the second end of the body;
a second restriction member extending from a proximal end to a distal end along a second restriction member axis, wherein the proximal end is coupled to the body and the distal end extends into the second bore towards the first end of the body;
wherein the suture element extends through the second bore such that the distal end of the second restriction member extends into the second bore to restrict the ligating element from moving within the second bore from the first end of the body to the second end of the body.

11. The system of claim 1, wherein the distal end of the first restriction member is located less than 0.010 inch or less away from the control element of the suture element.

12. The system of claim 1, wherein the first restriction member axis and the first bore axis form an included angle of about 75 degrees or less, and wherein the distal end restricts the suture element located within the first bore from moving within the first bore from the first end of the body to the second end of the body.

13. The system of claim 12, wherein the suture lock body comprises:
a second bore extending along a second bore axis from the first end of the body to the second end of the body; and
a second restriction member extending from a proximal end to a distal end along a second restriction member axis, wherein the proximal end is coupled to the body and the distal end extends into the second bore towards the first end of the body, wherein the second restriction member axis and the second bore axis form an included angle of about 75 degrees or less, wherein the suture element extends through the second bore of the suture lock, and wherein the distal end restricts the suture element located within the second bore from moving within the second bore from the first end of the body to the second end of the body.

14. The system of claim 1, wherein the distal end is located at a first distance across the first bore that is about 50% or less than the width of the first bore, wherein the distal end restricts the suture element located within the first bore from moving within the first bore from the first end of the body to the second end of the body.

15. The system of claim 14, wherein the first distance is about 40% or less across the width of the first bore diameter.

16. The system of claim 14, wherein the first distance is about 33% or less across the width of the first bore diameter.

17. The system of claim 14, wherein the suture lock body comprises:
a second bore extending through the body from the first end of the body to the second end of the body; and
a second restriction member extending from a proximal end to a distal end, wherein the proximal end is coupled to the body and the distal end extends into the second bore towards the first end of the body, wherein the distal end is located at a second distance across the second bore that is about 50% or less than the width of the second bore, wherein the suture element extends through the second bore of the suture lock, and wherein the distal end restricts the suture element located within the second bore from moving within the second bore from the first end of the body to the second end of the body.

18. A suture system comprising:
a suture lock comprising:
a body extending from a first end to a second end;
a first bore extending along a first bore axis from the first end of the body to the second end of the body, and
a first restriction member extending from a proximal end to a distal end along a first restriction member axis, wherein the proximal end is coupled to the body and the distal end extends into the first bore towards the first end; and
a suture element extending through the first bore of the suture lock, wherein the suture element comprises:
a ligating element extending from a first end of the suture element to a second end of the suture element,
a lumen extending through the ligating element, and
a control element located within and extending through the lumen of the ligating element, wherein the control element is incompressible,
wherein the distal end of the first restriction member pierces the ligating element of the suture element within the first bore to restrict the ligating element from moving within the first bore from the first end of the body to the second end of the body.

19. A suture system comprising:
a suture lock comprising:
a body extending from a first end to a second end;
a first bore extending along a first bore axis from the first end of the body to the second end of the body, and
a first restriction member extending from a proximal end to a distal end along a first restriction member axis, wherein the proximal end is coupled to the body and the distal end extends into the first bore towards the first end; and a suture element extending through the first bore of the suture lock, wherein the suture element comprises:
  a ligating element extending from a first end of the suture element to a second end of the suture element,
  a lumen extending through the ligating element, and
  a control element located within and extending through the lumen of the ligating element, wherein the control element is incompressible, wherein the suture lock includes only one substantially rigid restriction member extending into the first bore and in contact with only one side of the ligating element in the first bore to restrict the ligating element from moving within the first bore from the first end of the body to the second end of the body, and wherein the distal end of the first restriction member extends into an interstice between filaments forming the ligating element.

20. The system of claim 19, wherein the system further comprises:
  a second bore extending through the body of the suture lock along a second bore axis from the first end of the body to the second end of the body;
  a second restriction member extending from a proximal end to a distal end along a second restriction member axis, wherein the proximal end is coupled to the body and the distal end extends into the second bore towards the first end of the body;
  wherein the suture element extends through the second bore such that the distal end of the second restriction member contacts the ligating element within the second bore to restrict the ligating element from moving within the second bore from the first end of the body to the second end of the body;
  and wherein the suture lock includes only one restriction member extending into the second bore and in contact with only one side of the ligating element in the second bore to restrict the ligating element from moving within the second bore from the first end of the body to the second end of the body.

21. A suture system comprising:
  a suture lock comprising:
    a body extending from a first end to a second end;
    a first bore extending along a first bore axis from the first end of the body to the second end of the body, and
    a first restriction member extending from a proximal end to a distal end along a first restriction member axis, wherein the proximal end is coupled to the body and the distal end extends into the first bore towards the first end; and
  a suture element extending through the first bore of the suture lock, wherein the suture element comprises:
    a ligating element extending from a first end of the suture element to a second end of the suture element,
    a lumen extending through the ligating element, and
    a control element located within and extending through the lumen of the ligating element, wherein the control element is incompressible,
  wherein the suture lock includes only one substantially rigid restriction member extending into the first bore and in contact with only one side of the ligating element in the first bore and the distal end of the first restriction member pierces the ligating element of the suture element to restrict the ligating element from moving from the first end to the second end of the first bore.

22. The system of claim 21, wherein the system further comprises:
  a second bore extending through the body of the suture lock along a second bore axis from the first end of the body to the second end of the body;
  a second restriction member extending from a proximal end to a distal end along a second restriction member axis, wherein the proximal end is coupled to the body and the distal end extends into the second bore towards the first end of the body;
  wherein the suture element extends through the second bore such that the distal end of the second restriction member contacts the ligating element within the second bore to restrict the ligating element from moving within the second bore from the first end of the body to the second end of the body;
  and wherein the suture lock includes only one restriction member extending into the second bore and in contact with only one side of the ligating element in the second bore to restrict the ligating element from moving within the second bore from the first end of the body to the second end of the body.

\* \* \* \* \*